United States Patent [19]

Cox et al.

[11] Patent Number: 4,518,420

[45] Date of Patent: May 21, 1985

[54] WINNING METAL FROM ORE

[75] Inventors: Michael Cox, Hitchin; Michael J. Gray, Luton; Phillip W. Duke, Chester, all of England

[73] Assignee: National Research Development Corporation, London, England

[21] Appl. No.: 572,148

[22] Filed: Jan. 19, 1984

[30] Foreign Application Priority Data

Jan. 21, 1983 [GB] United Kingdom ................ 8301647

[51] Int. Cl.$^3$ .............................................. C22B 1/10
[52] U.S. Cl. ........................................... 75/26; 75/2; 75/101 R
[58] Field of Search ............................ 75/26, 2, 101

[56] References Cited

U.S. PATENT DOCUMENTS 1,789,813  1/1931  Gaus ................................... 423/133
4,123,260 10/1978  Sefton ............................ 75/101 BE
4,130,415 12/1978  Nagaraj ................................... 75/2

Primary Examiner—Peter D. Rosenberg
Attorney, Agent, or Firm—Cushman, Darby & Cushman

[57] ABSTRACT

Copper is won from chalcopyrite ore (copper/iron sulphide) containing Cu(II) and Fe(III), which respectively prefer square planar and octahedral co-ordination. A vaporized tetradentate (square-planar) Schiff base reagent is passed through a fluidized bed of oxidatively roasted chalcopyrite, and ignores the iron but forms a (volatile) copper complex. This is blown to a decomposition chamber containing a hot probe on which the complex decomposes, leaving the desired copper on the probe and liberating the Schiff base reagent for recycling.

17 Claims, No Drawings

WINNING METAL FROM ORE

The present invention relates to a method of winning metals from ore, preferably without chemical pretreatment, or from an enriched or partly treated ore or from a compound or compounds of the metal, in the presence of (an)other metal(s) as ore or compounds. All such forms of the metal (i.e. excluding its elemental state), preferably in the solid state, are hereinafter referred to as "ore" for brevity.

A process of winning one or more desired metals from an ore containing also at least one undesired metal comprises, according to the present invention, treating the ore with a (preferably volatile) polydentate reagent which forms a (preferably volatile) compound with the or each desired metal but not with the undesired metal(s), transporting (preferably in the vapour phase if possible) the compound from the vicinity of the ore, and decomposing the compound to liberate elemental metal. A polydentate reagent is one which reacts, using at least two functional groups of itself, to combine (e.g. to chelate or complex) with the metal, and must display a substantial stereochemical constraint on the metal, such as square planar. Its donor atoms may be any selection from N, O and S. It is preferably tetradentate, for example a phthalocyanine, a porphyrin, a Schiff base reagent or a hydroxyoxime. The reagent may undergo a subsidiary molecular interaction with itself whereby it applies to the metal a stereochemistry different from its formal stereochemistry. Thus, for example, hydroxyoxime, which is formally bidentate, dimerises to form an effectively tetradentate reagent.

The ore may be such that the desired metal(s) display(s) a different stereochemistry from the undesired metal(s), or the process may include a step of pretreating the ore so that the metals are in oxidation states in which they display different stereochemistries (e.g. the desired metal(s) can adopt a four-coordinate stereochemistry); for example, a copper/iron/sulphide ore from which copper is to be won may be roasted with the intention or producing Cu(II) and Fe(III), which respectively prefer square planar and octahedral co-ordination. The ore may anyway with advantage be converted to oxide before the treatment.

If the ore contains a plurality of metals combinable with the reagent, the process may further comprise, between the ore and the decomposition, separating the compounds, for example by selective fractionation (e.g. crystallisation, distillation).

The ore may be treated with the reagent in, for example, a fluidised bed, to which heat may be applied as necessary and which the reagent participates in fluidising. The decomposition may be by reduction, performed for example by a gas or gases such as hydrogen or water gas, which may participate in fluidising a bed of particles of the same metal as is to be liberated, the particles thus acting as deposition nuclei. The reducing gas may be separated from the recovered reagent to permit recycling, or they may be recycled to the ore without separation.

The invention will now be described by way of example.

The object will be to win copper from chalcopyrite ore (tetragonally crystallized sulphide of copper and iron) leaving the iron behind.

The reagents will be considered first.

Examples of tetradentate Schiff base reagents suitable for Cu(II) are

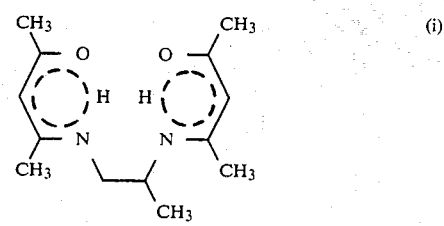

and

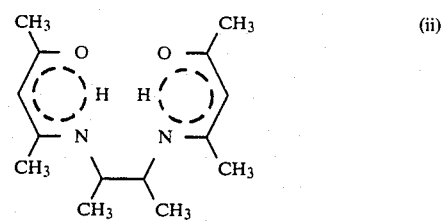

Iron, as Fe(III), prefers an octahedral co-ordination and is therefore not chelated by these reagents, whereas Cu(II) (square planar) is. These reagents may be synthesised as follows:

A Schiff base of general structure

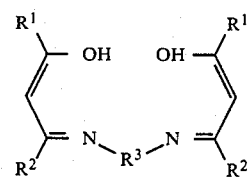

was prepared by condensing a β-diketone with a diamine, for example:

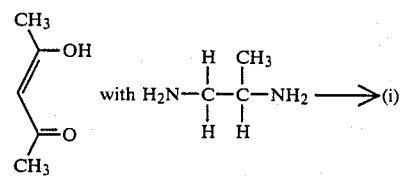

and

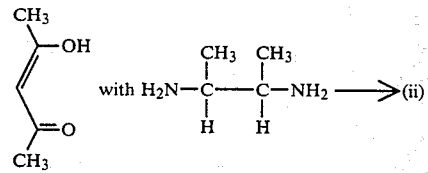

When both reactants were liquids the Schiff base could be prepared by adding them together undiluted in stoichiometric proportions. This reaction was found in most cases to be highly exothermic so that cooling was advisable and sometimes ethanol was used as a solvent. The latter was also the case if one or both of the reactants were solids. The ethanol, if used, was removed by reduced pressure rotary film evaporation. The products were recrystallised from ethanol. Copper complexes were prepared from the reagents. The preparation of iron(III) and iron(II) complexes was attempted without success, this being the desired outcome. The copper complexes were prepared by adding the reagent (ligand) to copper acetate in aqueous or ethanolic solution. Another technique was to reflux a solution of the ligand in acetone over freshly prepared copper hydroxide. More detailed trials on Reagent (i) proceeded as follows.

Reagent (i) was vaporised in a stream of nitrogen at 200° C. and the vapour passed through a fluidised bed of copper(II) sulphide at 150° C. An acidic "smoke" was driven off and analysis of the material in the column by thermogravimetry and thin layer chromatography indicated that most of the copper sulphide was unchanged, with some evidence of a little copper(II) complex.

The experiment was repeated but replacing the sulphide with copper(II) oxide. Most of Reagent (i) was retained in the column and analysis showed that a large amount of copper(II) complex was formed. However the fluidised bed temperature (150° C.) was not high enough to volatilise the complex.

A 1:1 mixture of copper(II) and iron(III) oxides was placed in the fluidised bed at a temperature of 240° C. A red-purple product was obtained after passage of reagent. This was shown by thermogravimetry and thin layer chromatography to consist of 80% iron(III) oxide and 20% copper(II) complex. The conclusion reached was that the vapour of the copper complex and the flowing nitrogen stream had physically carried over some very fine iron(III) oxide powder. No evidence was found of iron(III) complex indicating selective reaction with the copper.

Thermogravimetric data for Reagent (i), bis-acetylacetone proylenediamine ($H_2(pnAA_2)$), and Reagent (ii), bis-acetylacetone 2,3-butylenediamine ($H_2(2,3-bnAA_2)$), and their copper(II) complexes were obtained as follows:

fluidised). Here, the reagent reacted with the copper, forming square planar Cu(II) complex, and not with the iron.

The complex is sufficiently volatile not to condense at this temperature, and it leaves the furnace, borne on the nitrogen stream, through the outlet. In one run, for purposes of measurement, the outlet stream was cooled, and 2 g of solid product was obtained consisting of reagent, copper complex, water and 3% non-volatile material. In production, however, there would be no such cooling, except that if other metal complexes had been simultaneously formed, they would at this stage be subjected to a selective fractionation to separate the desired complex, such as by condensation or chromatography.

The copper complex was then passed (still as vapour, at 215° C. to 245° C.) into a decomposition chamber maintained generally at the same temperature but containing a hot probe which the vapour is constrained to pass, and optionally packed with glass beads (e.g. ½ mm, 3 mm or 8 mm) to provide a large heated surface. The hot probe was an electric heater enclosed in a silica glass sheath, and raised the temperature in its vicinity to (in one series) 200° C. to 390° C. or (in another) to 315° C. to 410° C. (all equally successful). In the presence of only nitrogen, the copper complex appeared stable. Hydrogen and nitrogen were also introduced (with the copper complex vapour) into the decomposition chambers. Because of the presence now of the hydrogen, the copper complex was reduced at the probe, where metallic copper plated out, purity>three nines. The gases leaving the decomposition chamber thus comprised liberated reagent, hydrogen and nitrogen. The reagent would be separated by any convenient method (e.g. condensation) and recycled to the extraction furnace, while the hydrogen and nitrogen could be returned to

|  | Reagent | | | Copper(II) Complex | | |
|---|---|---|---|---|---|---|
|  | % Wt Loss | Temp Range °C. of weight loss | T °C. at max DTG | % Wt Loss | Temp Range °C. of weight loss | T °C. at DTG |
| (i) a | 97 | 120–245 | 230 | 98 | 104–265 | 225 |
| (i) b | 96 | 105–250 | 235 | 98 | 100–260 | 230 |
| (ii) a | 99 | 110–280 | 215 | 88 | 115–310 | 260 |
| (ii) b | 98 | 105–280 | 210 | 90 | 105–290 | 255 |

Notes:
DTG = derivative thermogravimetric curve
Conditions a: 5° C. min$^{-1}$, ca. 7.5 μg b: 10° C. min$^{-1}$, ca. 2 μg We turn now to the overall process.

Chalcopyrite was oxidatively roasted by heating to 375° C. a fluidised bed of the chalcopyrite in a current of air. Sulphur dioxide was evolved and the reaction continued for 2 hours.

The oxidised (powdered) chalcopyrite was placed on a glass frit in an extraction furnace maintained at (in one series) 165° C. to 225° C. or (in another) at 200° C. to 250° C. and purged with nitrogen. The furnace has a gas outlet above the frit and a gas inlet below the frit. The chalcopyrite could be mixed with up to 100 times its volume of inert diluent, such as sand, which improved temperature control but at the cost of higher temperatures and longer running times.

Reagent (i) (m.p. 87° C.) was placed in a vessel heated to 160° C. to 220° C., in this case 190° C., and connected into the furnace gas inlet. Nitrogen, also heated to 190° C., was introduced through a diffuser into the molten reagent. Reagent vapour, borne by nitrogen, was thus swept into the gas inlet, through the frit and through the oxidised powdered chalcopyrite, (which was thereby the decomposition chamber; however, it was found more convenient simply to recirculate the hydrogen and nitrogen, with the reagent, to the extraction furnace. The hydrogen and nitrogen did not interfere with the extraction step, and could even be introduced to the process there.

Reagent (i) was applied in turn to nickel sulphide and to cobalt sulphide (not oxidatively roasted) by a similar procedure. Under reducing conditions, both metals were plated out at the hot probe. Since Reagent (i) forms no complex with iron, this offers a route to the removal of nickel and cobalt from iron/nickel/cobalt ores; the iron would be left behind.

In more detail, Reagent (i) was passed through a bed of Ni(II)S at 200° C., forming the Ni(II) complex, which was volatilised from the (fluidised) bed, transported in the vapour phase to a hot probe and reduced there at 250° C. to 350° C.; the carrier gas was a hydrogen:nitrogen mixture (1:6 by volume). Separately, Reagent (i) was passed through a bed of Co(II)S at 200° C., forming the Co(II) complex, which was volatilised from the (fluidised) bed, transported in the vapour phase to a hot probe and reduced there at 250° C. to 350° C.; the carrier gas was a hydrogen:nitrogen mixture (1:6 by volume).

We claim:

1. A process of winning one or more desired metals from an ore containing also at least one undesired metal, comprising the steps of:
    treating the ore with a polydentate reagent displaying a substantial stereochemical constraint on a metal, which reagent forms a volatile compound with the or each desired metal but not with the undesired metal(s);
    transporting the compound in the vapor phase from the vicinity of the ore; and
    decomposing the compound to literate elemental metal.

2. A process according to claim 1, wherein the reagent is a chelating or complexing reagent.

3. A process according to claim 1, wherein the ore is such that the desired metal(s) can adopt a different stereochemistry from the undesired metal(s).

4. A process according to claim 3, wherein the desired metal(s) can adopt a four-coordinate stereochemistry.

5. A process according to claim 1, further comprising after the treating but before the decomposition separating the compound(s) of some of the desired metal(s) from others.

6. A process according to claim 1, further comprising pre-treating the ore so that the metals are in oxidation states such that the metal(s) to be won can adopt a different stereochemistry from the undesired metal(s).

7. A process according to claim 1, further comprising the step of recovering the reagent from the decomposition of the compound(s) and recycling the recovered reagent to the ore.

8. A process according to claim 1, wherein the decomposition is by reduction.

9. A process according to claim 8, wherein the reduction is performed by a gas or gases.

10. A process according to claim 9, wherein the reducing gas participates in fluidising a bed of particles of the same metal as is to be liberated, the particles thus acting as deposition nuclei.

11. A process according to claim 1, wherein the reagent is volatile.

12. A process according to claim 11, wherein the treating of the ore is in a fluidised bed, which the reagent participates in fluidising.

13. A process according to claim 1, wherein the donor atoms of the said reagent at any selection from N, O and S.

14. A process according to claim 1, wherein the said reagent is tetradentate.

15. A process according to claim 1, wherein the said reagent is a hydroxyoxime, a porphyrin or a phthalocyanine.

16. A process according to claim 1, wherein the said reagent is a Schiff base reagent.

17. A process according to claim 16, wherein the said reagent is bis-acetylacetone propylenediamine or bis-acetylacetone 2,3,-butylenediamine.

* * * * *